US011368160B2

(12) United States Patent
Tseng et al.

(10) Patent No.: US 11,368,160 B2
(45) Date of Patent: Jun. 21, 2022

(54) NON-CONTACT PHASE-LOCKED AND SELF-INJECTION-LOCKED VITAL SIGN SENSOR

(71) Applicant: National Taiwan University of Science and Technology, Taipei (TW)

(72) Inventors: Chao-Hsiung Tseng, New Taipei (TW); Li-Te Yu, Yilan County (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 719 days.

(21) Appl. No.: 16/402,301

(22) Filed: May 3, 2019

(65) Prior Publication Data

US 2020/0313680 A1 Oct. 1, 2020

(30) Foreign Application Priority Data

Apr. 1, 2019 (TW) ................................. 108111482

(51) Int. Cl.
*A61B 5/05* (2021.01)
*H03L 7/093* (2006.01)
(Continued)

(52) U.S. Cl.
CPC .............. *H03L 7/093* (2013.01); *G01S 7/282* (2013.01); *G01S 13/88* (2013.01); *H01Q 1/24* (2013.01);
(Continued)

(58) Field of Classification Search
CPC ......... H03L 7/093; H03L 7/099; G01S 7/282; G01S 13/88; G01S 7/415; G01S 13/40;
(Continued)

(56) References Cited

U.S. PATENT DOCUMENTS

2012/0209087 A1* 8/2012 Horng ..................... G01S 13/87
  600/301
2012/0235689 A1* 9/2012 Jau .......................... G01S 13/88
  324/629
2016/0192084 A1* 6/2016 Oliaei .................. H04R 19/005
  367/135

FOREIGN PATENT DOCUMENTS

TW       I642406       12/2018
WO    WO-2010043992 A1 *  4/2010 ................ H03J 7/02

OTHER PUBLICATIONS

Tseng, Chao-Hsiung and Yu, Li-Te, "Self-Injection-Locked AIA Radar Sensor Using PLL Demodulator for Noncontract Vital Sign Detection", Jun. 12, 2018, Publication: International microwave symposium.

* cited by examiner

*Primary Examiner* — Tanmay K Shah
(74) *Attorney, Agent, or Firm* — WPAT, PC

(57) ABSTRACT

A non-contact phase-locked and self-injection-locked vital sign sensor includes a self-oscillating voltage-controlled frequency-adjustable radiating element and a phase-locked loop. The self-oscillating voltage-controlled frequency-adjustable radiating element is used for transmitting an oscillation signal to an organism and for receiving a corresponding reflected signal from the organism to be posed at a self-injection-locked state, the oscillation signal being tuned by a vital sign of the organism to form a frequency-tuned signal. The phase-locked loop is used for demodulating the frequency-tuned signal to obtain a corresponding vital signal of the organism. By comparing the oscillation signal frequency-eliminated and outputted from the self-oscillating voltage-controlled frequency-adjustable radiating element with a reference signal, a corresponding comparison result is used to vary a phase of the frequency-divided oscillation (Continued)

signal for maintaining the same phase of the reference signal. Thereupon, the oscillation frequency can be stabilized, and the measurement sensitivity can be enhanced.

10 Claims, 3 Drawing Sheets

(51) Int. Cl.
*H02M 3/07* (2006.01)
*H04L 27/152* (2006.01)
*H01Q 1/24* (2006.01)
*G01S 13/88* (2006.01)
*G01S 7/282* (2006.01)
*H04L 7/033* (2006.01)
*A61B 5/11* (2006.01)
*A61B 5/024* (2006.01)
*A61B 5/08* (2006.01)

(52) U.S. Cl.
CPC ............ *H02M 3/07* (2013.01); *H04L 7/0331* (2013.01); *H04L 27/152* (2013.01); *A61B 5/024* (2013.01); *A61B 5/0816* (2013.01); *A61B 5/11* (2013.01)

(58) Field of Classification Search
CPC .......... G01S 13/536; H01Q 1/24; H02M 3/07; H04L 7/0331; H04L 27/152; A61B 5/024; A61B 5/0816; A61B 5/11; A61B 5/0507; A61B 5/7225
USPC ....................................... 600/430
See application file for complete search history.

NON-CONTACT PHASE-LOCKED AND SELF-INJECTION-LOCKED VITAL SIGN SENSOR

CROSS REFERENCE TO RELATED APPLICATION

This application claims the benefit of Taiwan Patent Application Serial No. 108111482, filed on Apr. 1, 2019, the subject matter of which is incorporated herein by reference.

BACKGROUND OF THE INVENTION

(1) Field of the Invention

The invention relates to a non-contact phase-locked and self-injection-locked vital sign sensor, and more particularly to the non-contact phase-locked and self-injection-locked vital sign sensor that is characterized by a small size, a lower cost and a lockable frequency, such that the frequency can be stabilized and adjustable and the measurement sensitivity can be kept high.

(2) Description of the Prior Art

The wearable vital or physiological sign sensor for detecting breathing, heart beats and pulses is one of personal electronic devices with prosperous development potential. Currently, the wearable vital or physiological sign sensor usually applies a photoelectric sensing method to perform detection of vital or physiological signals. In the art, the photoelectric sensing method introduces a light beam to radiate a human skin, so that the photoelectric components therein can capture and/or observe variations of light intensity. If the light intensity is detected, it implies that a blood volume at the corresponding skin is changed. In other words, the heart is experienced a cardiac contraction then, and thereupon a corresponding heart rate can be detected.

Since the conventional photoelectric sensing method is sensitive to environmental lights, thus the photoelectric sensor shall be adhered firmly to the human skin, so that accurate vital signals at the interested skin can be obtained. Hence, the design of the vital sign sensor can't be versatile. For example, a majority of the vital sign sensors in the marketplace are in a form of wrist watch. In addition, since the vital sign sensor shall be firmly adhered to the skin, a long-term usage of this wrist type of the vital sign sensor would cause discomfort to the user.

Further, while the sensor is detecting vital signals of a human body, a frequency of reflected signals to the sensor would be affected anyway by breathing, beating and pulsing of the human body. Even that the concerned vibrations of the human body are extremely minor, detection errors at the vital signals would be induced to lower the corresponding measurement sensitivity.

In addition, in view of patents related to the vital sign sensors such as a self-injection-locked radar, a frequency discriminator for demodulation is usually applied as a modulation mechanism. Typically, the demodulation mechanism is consisted of a mixer, a delay line and a power splitter. In the art, the delay line is a meter-long coaxial cable, and thus the occupation cannot be neglected. Further, circuit components for the frequency discriminator are generally expansive. Nevertheless, some other patents of the vital sign sensors apply the conventional homodyne radar, which a larger number of sensor elements is needed. Thus, the price of this type of the vital sign sensors is hard to be reduced, but the performance thereof is poorer than that of the self-injection-locked radar. Related documents to reveal the aforesaid discussions are already available to the public.

In addition, in a Taiwan patent titled as a non-contact disturbance sensing device, two antennas, one for transmitting while another for receiving, are introduced to pair an oscillator. In this patent, the transmitting antenna sends a wireless signal to a human body, and then the receiving antenna receives a reflected signal from the human body. The reflected signal is then forwarded to the oscillator so as to generate an oscillation signal, and a phase-locked loop evaluates the oscillation signal to generate a control voltage.

Obviously, in the aforesaid patent, the framework of two antennas, an oscillator and a phase-locked loop is comparative huge and complicated, and thus the related cost is too high to be relevant for the mainstream trend of miniaturization.

Thus, a non-contact phase-locked and self-injection-locked vital sign sensor characterized by a light volume, a lower cost and a lockable frequency, so that the frequency can be stabilized and adjustable and the measurement sensitivity can be kept high, is urgent and welcome to the art.

SUMMARY OF THE INVENTION

Accordingly, in an embodiment of the present invention, a non-contact phase-locked and self-injection-locked vital sign sensor includes:

a self-oscillating voltage-controlled frequency-adjustable radiating element, used for transmitting an oscillation signal to an organism and for receiving a corresponding reflected signal from the organism to be posed at a self-injection-locked state, the oscillation signal being tuned by a vital sign of the organism to form a frequency-tuned signal; and a phase-locked loop, used for demodulating the frequency-tuned signal to obtain a corresponding vital signal of the organism; wherein, by comparing the oscillation signal frequency-divided and outputted from the self-oscillating voltage-controlled frequency-adjustable radiating element with a reference signal, a corresponding comparison result is used to vary a phase of the frequency-divided oscillation signal for maintaining the same phase of the reference signal.

In another embodiment of the present invention, a system having a non-contact phase-locked and self-injection-locked vital sign sensor includes:

a base-band amplifier, electrically coupled with an output port of the phase-locked loop, used for receiving and amplifying the vital signal;

an analog-to-digital converter, electrically coupled with the base-band amplifier, used for receiving the amplified vital signal and further transforming the analog vital signal into a corresponding digital vital signal; and a signal-processing device, electrically coupled with the analog-to-digital converter, used for receiving and processing the digital vital signal.

All these objects are achieved by the non-contact phase-locked and self-injection-locked vital sign sensor described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a non-contact phase-locked and self-injection-locked vital sign sensor. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
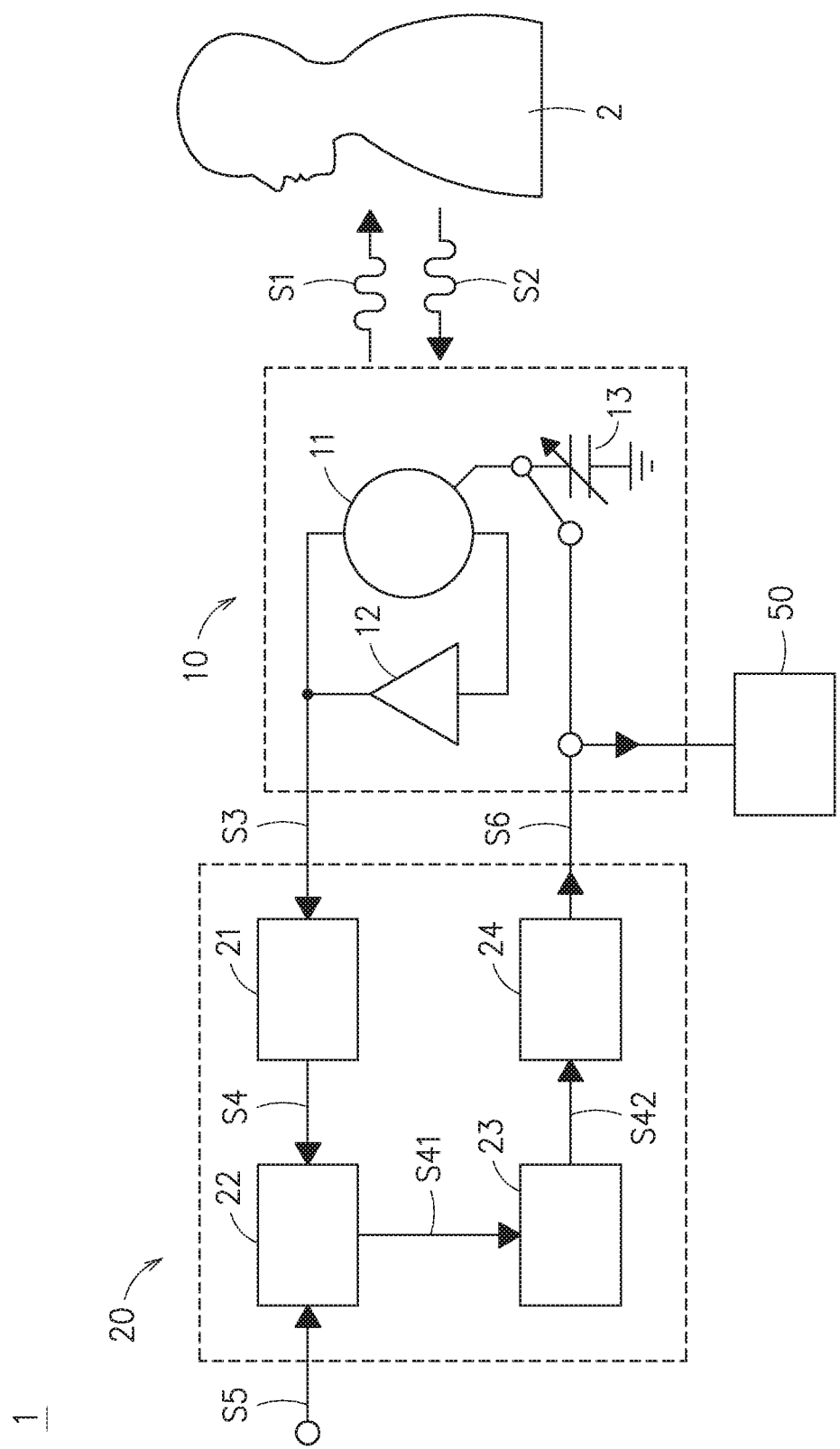
FIG. 1 is a schematic view of an embodiment of the non-contact phase-locked and self-injection-locked vital sign sensor in accordance with the present invention.

Referring now to FIG. 1, the non-contact phase-locked and self-injection-locked vital sign sensor 1, provided by this invention, includes a self-oscillating voltage-controlled frequency-adjustable radiating element 10 and a phase-locked loop 20.

As shown in FIG. 1, the self-oscillating voltage-controlled frequency-adjustable radiating element 10 is used for transmitting an oscillation signal S1 to an organism 2 such as a human body, and then for receiving a reflected signal S2 from the organism S, and now is at a self-injection-locked state. The oscillation signal S1 is tuned by a vital sign (i.e., a physiological sign) of the organism 2 to form a frequency-tuned signal S3. In the present invention, the embodying of the self-oscillating voltage-controlled frequency-adjustable radiating element 10 is not limited to the aforesaid embodiment. For example, the self-oscillating voltage-controlled frequency-adjustable radiating element 10 can be one of the self-oscillating active antenna and the active near-field sensor, from which far-field (over 1 centimeter) and/or near-field (less than 1 centimeter) measurements between the self-oscillating voltage-controlled frequency-adjustable radiating element 10 and the organism 2 can be performed.

To achieve the foregoing object, it is understood that the framework of the self-oscillating voltage-controlled frequency-adjustable radiating element 10 is not specifically limited to the aforesaid embodiment shown in FIG. 1. However, in this embodiment, the self-oscillating voltage-controlled frequency-adjustable radiating element 10 includes an antenna 11, an active amplification component 12 and a variable capacitor 13.

The antenna 11 is to transmit the oscillation signal S1 with a predetermined frequency to the organism 2, and then the organism 2 produces a corresponding reflected signal S2 to be transmitted to and thus received by the antenna 11, such that the self-oscillating voltage-controlled frequency-adjustable radiating element 10 is posed at a self-injection-locked state. In this embodiment, the oscillation signal 1 is tuned by a vital sign of the organism 2 to form a frequency-tuned signal S3.

The active amplification component 12 is electrically coupled with the antenna 11. With the antenna 11 and the active amplification component 12, the oscillation signal S1 can be induced. In the present invention, the embodying of the active amplification component 12 is not limited to this embodiment. For example, the active amplification component 12 can be a solid-state amplifier, a bipolar junction transistor (BJT) amplifier, a field-effect transistor (FET) amplifier, an amplifier integrated circuit or a transistor amplifier.

The variable capacitor 13, electrically coupled with antenna 11, is to apply different voltages for the antenna 11 to select or determine an operating frequency.

For other aspects and detail operations of the antenna 11 and the active amplification component 12, please refer to the granted Taiwan Patent "Non-Contact Self-Injection-Locked Sensor", having a patent publication no. 1642406 dated on Dec. 1, 2018, and a patent application no. 106143627 filed on Dec. 12, 2017, under the same applicant as this present invention. In this present invention, the variable capacitor 13, electrically coupled with antenna 11, furnishes the self-oscillating voltage-controlled frequency-adjustable radiating element 10 with a voltage-controlled frequency-adjustable feature. However, it shall be explained that resort for achieving voltage controllability and frequency adjustability is not limited to the aforementioned variable capacitor 13.

As shown in FIG. 1, the phase-locked loop 20 is used for receiving the frequency-tuned signal S3, and further for demodulating the frequency-tuned signal S3 to obtain a corresponding vital signal of the organism 2. The phase-locked loop 20 is also used to compare the frequency-divided oscillation signal S4 with a reference signal S5. Based on the comparison result, a corresponding tuned voltage is generated to tune the oscillation frequency back to the setting frequency, and thus the foregoing feedback control or calibration can bring the self-oscillating voltage-controlled frequency-adjustable radiating element 10 back to a state that the oscillation signal and the reference signal S5 are maintained at the same phase.

In the present invention, to achieve the aforementioned functions, the embodying of the phase-locked loop 20 is not limited to the embodiment of FIG. 1. In this embodiment, the phase-locked loop 20 includes a frequency divider 21, a phase detector 22, a charge pump 23 and a loop filter 24.

The frequency divider 21 is used for receiving the frequency-tuned signal S3, and for frequency-dividing the frequency-tuned signal S3 so as to obtain a frequency-dividing oscillation signal S4.

The phase detector 22 is used for receiving the frequency-divided oscillation signal S4 and the reference signal S5, and for comparing the frequency-divided oscillation signal S4 with the reference signal S5. Based on the comparison result to generate a tuned voltage, then the oscillation frequency can be tuned back to the setting frequency, and thereby a feedback control can be performed upon the self-oscillating voltage-controlled frequency-adjustable radiating element 10, such that the oscillation signal and the reference signal S5 can be kept at the same phase.

The charge pump 23 is used for receiving the output signal S41 of the phase detector, and further for transforming the output signal S41 of the phase detector into a corresponding current signal S42.

The loop filter 24 is used for receiving the current signal S42, and further for transforming the current signal S42 into a corresponding analog voltage signal S6. After being filtered out high-frequency noises, the analog voltage signal S6 is forwarded to a signal-processing device 50 and the self-oscillating voltage-controlled frequency-adjustable radiating element 10.

By having the signal-processing device 50 to process the tuned voltage, the vital signal of the organism 2 can be thus obtained. In other words, the tuned voltage stands for the vital signal of the organism 2.

It shall be emphasized that, though recent applications of the phase-locked loop 20 become popular, yet specific applications in detecting vital signals are still not common. In particular, due to structural limitations, previous patents for detecting vital signals need two antennas to pair an oscillator, and thus a big complicated structure and a higher cost may be inevitable. On the other hand, the present invention utilizes the self-oscillating voltage-controlled frequency-adjustable radiating element 10 and the phase-locked loop 20 to form an integrated framework, in which the self-oscillating voltage-controlled frequency-adjustable radiating element 10 is exactly the same self-injection-locked integrated oscillation antenna of the granted Taiwan Patent "Non-Contact Self-Injection-Locked Sensor", having a patent publication no. I642406 dated on Dec. 1, 2018, and a patent application no. 106143627 filed on Dec. 12, 2017, under the same applicant as this present invention. The self-injection-locked integrated oscillation antenna is furnished integrally to perform oscillations, signal emitting and signal receiving. Namely, in the self-injection-locked state, amplitude modulation and frequency modulation of the vital signs with respect to the antenna signals can be obtained simultaneously. Thus, detections of the vital signals can be performed with much more sensitivity and precision. More importantly, in comparison with the previous patents, the present invention can reduce significantly the structural complicity and the cost. In other words, the applicant of this present invention is fully aware of the aforesaid insufficiency at the foregoing patents, and thus encouraged to provide an improvement for the patented non-contact self-injection-locked sensor. The improvement is the non-contact phase-locked and self-injection-locked vital sign sensor of the present invention. Since the frequency is lockable, thus the noise level can be lowered, and therefore the vital signal won't be missed. Also, since the sensitivity has been improved, thus the present invention can detect various vital signals such as heart beats, breathing, pulses, and minor vital signals such as those at the finger tips.

Figure 2:
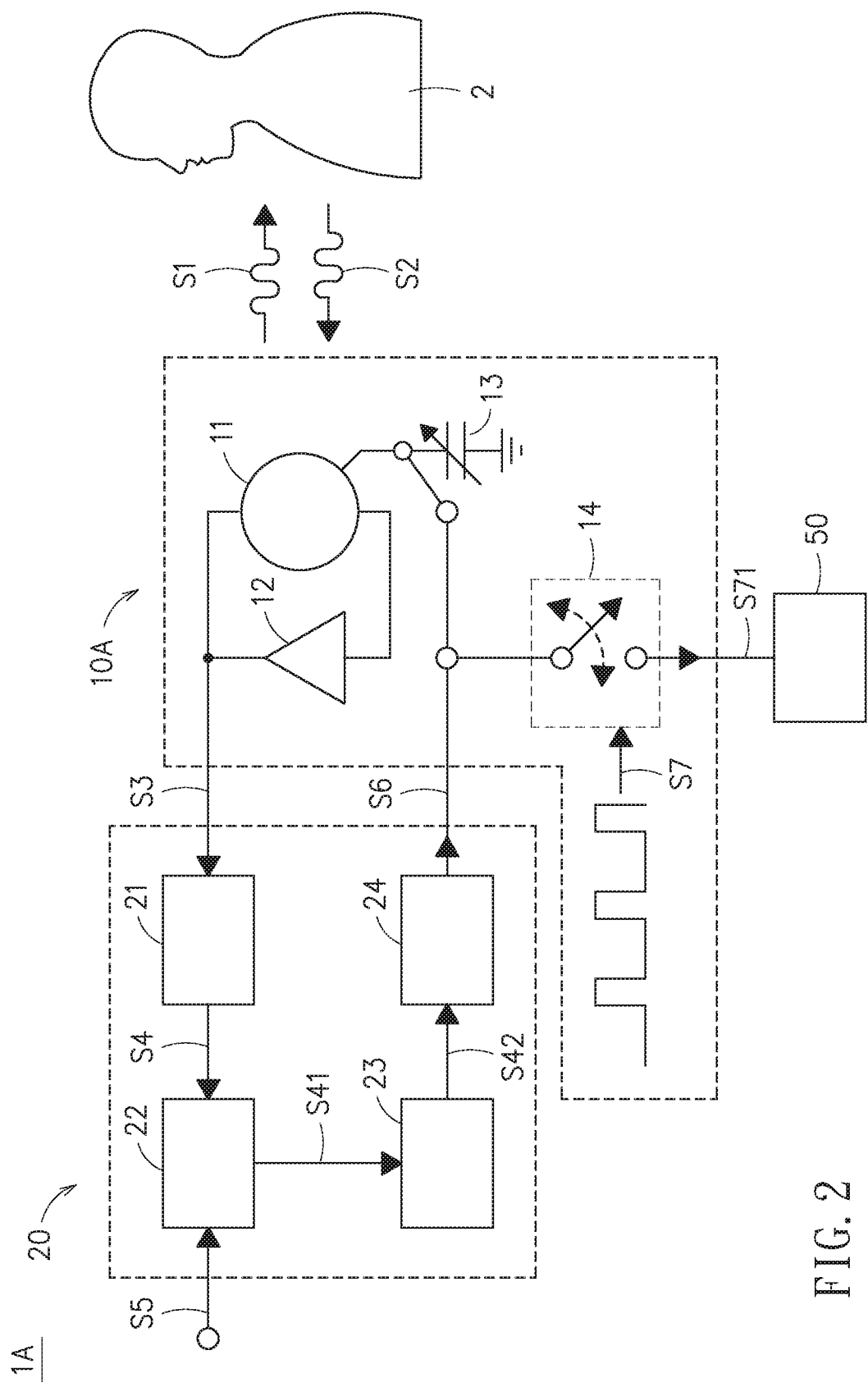
FIG. 2 is a schematic view of another embodiment of the non-contact phase-locked and self-injection-locked vital sign sensor in accordance with the present invention.

Referring now to FIG. 2, in this embodiment, the non-contact phase-locked and self-injection-locked vital sign sensor 1A includes a self-oscillating voltage-controlled frequency-adjustable radiating element 10A and a phase-locked loop 20. This embodiment 1A is largely resembled to that shown in FIG. 1, but a major difference is that, in this embodiment of FIG. 2, a switch 14 is furnished between the phase-locked loop 20 and the self-oscillating voltage-controlled frequency-adjustable radiating element 10A. The switch 14, electrically coupled with a signal-processing device 50, receives a control signal S7 (sent from the signal-processing device 50 or another signal-processing device) for switching so as to generate a low intermediate frequency (IF) signal S71. The low IF signal S71 is transmitted to the signal-processing device 50, and is processed there to obtain a corresponding vital signal having an in-phase I signal channel and a quadrature Q signal channel.

The self-oscillating voltage-controlled frequency-adjustable radiating element 10A includes an antenna 11, an active amplification component 12 and a variable capacitor 13. The antenna 11 transmits an oscillation signal S1 to the organism 2. The organism 2 receives the oscillation signal S1, and then generates a reflected signal S2 to be received by the antenna 11. Thereupon, the self-oscillating voltage-controlled frequency-adjustable radiating element 10A is posed at a self-injection-locked state. Also, the oscillation signal S1 is tuned to be a frequency-tuned signal S3 by a vital sign of the organism 2. The variable capacitor 13 is used for receiving different voltages so as to produce variant frequencies for the antenna 11 to select.

The phase-locked loop 20 includes a frequency divider 21, a phase detector 22, a charge pump 23 and a loop filter 24. The frequency divider 21 is used for receiving the frequency-tuned signal S3, and for generating an oscillation signal S4 after frequency-dividing the frequency-tuned signal S3. The phase detector 22 for receiving the frequency-divided oscillation signal S4 and a reference signal S5 is to compare the frequency-divided oscillation signal S4 and the reference signal S5. By evaluating a comparison result from comparing the frequency-divided oscillation signal S4 and the reference signal S5, a corresponding tuned voltage is generated for feedback controlling the self-oscillating voltage-controlled frequency-adjustable radiating element 10A so as to maintain the same phase with the reference signal S5. The charge pump 23 is used for receiving a phase detector output signal S41, and for transforming the phase detector output signal S41 into a corresponding current signal S42. The loop filter 24 is used for transforming the current signal S42 into a corresponding analog-voltage signal S6. After high-frequency noises within the analog-voltage signal S6 are filtered out, the analog-voltage signal S6 is forwarded to both the switch 30 and the self-oscillating voltage-controlled frequency-adjustable radiating element 10A. The analog voltage signal S6 is further transmitted to the signal-processing device 50 via the switch 14. As described above, the switch 14 is to generate a low IF signal for the signal-processing device 50 to demodulate and further recognize the in-phase (I) channel signal the quadrature (Q) channel signal, so that null detection points during sensing can be avoided.

Figure 3:
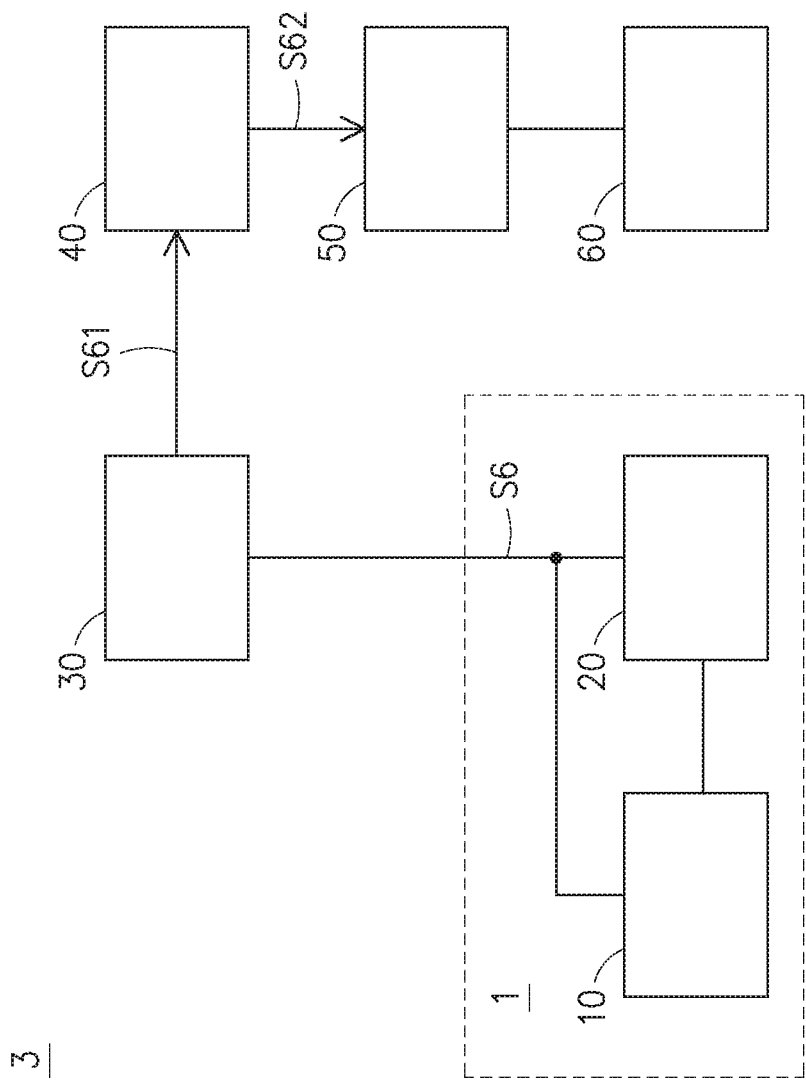
FIG. 3 is a schematic view of a system having the non-contact phase-locked and self-injection-locked vital sign sensor of FIG. 1.

Referring now to FIG. 3, a system 3 having the aforesaid non-contact phase-locked and self-injection-locked vital sign sensor 1 of FIG. 1 or 1A of FIG. 2 is schematically shown. In this embodiment, the system 3 applies the non-contact phase-locked and self-injection-locked vital sign sensor 1 of FIG. 1 for concise explanation.

As shown in FIG. 1 and FIG. 3, the system 3 includes a non-contact phase-locked and self-injection-locked vital sign sensor 1, a base-band amplifier 30, an analog-to-digital converter 40 and a signal-processing device 50.

The base-band amplifier 30, electrically coupled with an output port of the phase-locked loop 20, is used for receiving and amplifying the vital signal S6.

The analog-to-digital converter 40, electrically coupled with the base-band amplifier 30, is used for receiving an amplified vital signal S61 and further transforming the analog vital signal S61 into a corresponding digital vital signal S62.

The signal-processing device 50, electrically coupled with the analog-to-digital (A/D) converter 40, is used for receiving and further processing the digital vital signal S62. In this embodiment, the signal-processing device 50 can be a computer or a micro controller.

The frequency divider 21, the phase detector 22 and the charge pump 23 are integrated to form an integrated circuit. This integrated circuit is furnished with a plurality of leads to electrically couple the signal-processing device 50, so that the signal-processing device 50 can control the integrated circuit through a transmission interface 60.

In summary, the non-contact phase-locked and self-injection-locked vital sign sensor provided by the present invention includes a self-oscillating voltage-controlled frequency-adjustable radiating element and a phase-locked loop. A radiant component of the self-oscillating voltage-controlled frequency-adjustable radiating element is to perform both the signal transceiving and the frequency selection, which is different to the conventional antenna of the vital sign sensor that is used only for signal transceiving. The phase-locked loop is also to serve for stabilizing signals as a self-oscillating active antenna (by lowering the phase noise level) and for demodulating the vital-sign signals. It is understood that the conventional vital-sign sensor is seldom furnished with a framework like the phase-locked loop. Even the conventional vital-sign sensor is furnished with a phase-locked loop, the entire structuring is cumbersome and complicated. Since most of major elements of the present invention can perform multiple functions, thus, in comparison with the conventional vital-sign sensor, the present invention can lock the frequency and thus stabilize the frequency, so that the measurement sensitivity can be kept high. In addition, since the number of elements is reduced, thus the total cost can be lowered, the circuit complicity can be decreased, and so both the size and the price can be reduced.

While the present invention has been particularly shown and described with reference to a preferred embodiment, it will be understood by those skilled in the art that various changes in form and detail may be without departing from the spirit and scope of the present invention.

What is claimed is:

1. A non-contact phase-locked and self-injection-locked vital sign sensor, comprising:
    a self-oscillating voltage-controlled frequency-adjustable radiating element, used for transmitting an oscillation signal to an organism and for receiving a corresponding reflected signal from the organism to be posed at a self-injection-locked state, the oscillation signal being tuned by a vital sign of the organism to form a frequency-tuned signal; and
    a phase-locked loop, used for demodulating the frequency-tuned signal to obtain a corresponding vital signal of the organism; wherein, by comparing the oscillation signal frequency-divided and outputted from the self-oscillating voltage-controlled frequency-adjustable radiating element with a reference signal, a corresponding comparison result is used to vary a phase of the frequency-divided oscillation signal for maintaining the same phase of the reference signal.

2. The non-contact phase-locked and self-injection-locked vital sign sensor of claim 1, wherein the self-oscillating voltage-controlled frequency-adjustable radiating element includes:
    an antenna, used for frequency selection, transmitting the oscillation signal to the organism, and receiving a reflected signal reflected by the organism so that the self-oscillating voltage-controlled frequency-adjustable radiating element is posed at a self-injection-locked state, the oscillation signal being tuned by the vital sign of the organism to form the frequency-tuned signal;
    an active amplification component, electrically coupled with the antenna, the oscillation signal being induced by the antenna and the active amplification component; and
    a variable capacitor, electrically coupled with the antenna, used for applying different voltages to vary an operating frequency of the antenna.

3. The non-contact phase-locked and self-injection-locked vital sign sensor of claim 1, wherein the active amplification component is one of a solid-state amplifier, a bipolar junction transistor (BJT) amplifier, a field-effect transistor (FET) amplifier, an amplifier integrated circuit and a transistor amplifier.

4. The non-contact phase-locked and self-injection-locked vital sign sensor of claim 1, wherein the phase-locked loop includes:
    a frequency divider, used for receiving the frequency-tuned signal, and for frequency-dividing the frequency-tuned signal so as to obtain the frequency-divided oscillation signal;
    a phase detector, used for receiving the frequency-divided oscillation signal and the reference signal, for comparing the frequency-divided oscillation signal with the reference signal, and for, based on the comparison result, generating a tuned voltage to feedback control the self-oscillating voltage-controlled frequency-adjustable radiating element so as to keep the same phase as the reference signal;
    a charge pump, used for receiving an output signal of the phase detector and further transforming the output signal of the phase detector into a corresponding current signal; and
    a loop filter, used for receiving the current signal and further transforming the current signal into a corresponding analog voltage signal with high-frequency noises being filtered out, the analog voltage signal being transmitted to both a signal-processing device and the self-oscillating voltage-controlled frequency-adjustable radiating element.

5. The non-contact phase-locked and self-injection-locked vital sign sensor of claim 1, further including a switch disposed between the phase-locked loop and the self-oscillating voltage-controlled frequency-adjustable radiating element, the switch receiving a control signal for switching, the vital control signal being processed to obtain the vital signal having an in-phase (I) signal channel and a quadrature (Q) signal channel.

6. The non-contact phase-locked and self-injection-locked vital sign sensor of claim 1, wherein the self-oscillating voltage-controlled frequency-adjustable radiating element is one of the self-oscillating active antenna and an active near-field sensor.

7. A system having the non-contact phase-locked and self-injection-locked vital sign sensor of claim 1, comprising:
    a base-band amplifier, electrically coupled with an output port of the phase-locked loop, used for receiving and amplifying the vital signal;
    an analog-to-digital converter, electrically coupled with the base-band amplifier, used for receiving the amplified vital signal and further transforming the analog vital signal into a corresponding digital vital signal; and
    a signal-processing device, electrically coupled with the analog-to-digital converter, used for receiving and processing the digital vital signal.

8. The system having the non-contact phase-locked and self-injection-locked vital sign sensor of claim 7, wherein the signal-processing device is one of a computer and a micro controller.

9. The system having the non-contact phase-locked and self-injection-locked vital sign sensor of claim 7, wherein the phase-locked loop includes:
    a frequency divider, used for receiving the frequency-tuned signal and frequency-dividing the frequency-tuned signal to obtain the frequency-divided oscillation signal;

a phase detector, used for receiving the frequency-divided oscillation signal and the reference signal, for comparing the frequency-divided oscillation signal with the reference signal, and for, based on the comparison result, generating a tuned voltage to feedback control the self-oscillating voltage-controlled frequency-adjustable radiating element so as to keep the same phase as the reference signal;

a charge pump, used for receiving an output signal of the phase detector and further transforming the output signal of the phase detector into a corresponding current signal; and a loop filter, used for receiving the current signal and further transforming the current signal into a corresponding analog voltage signal with high-frequency noises being filtered out, the analog voltage signal being transmitted to both a signal-processing device and the self-oscillating voltage-controlled frequency-adjustable radiating element.

10. The system having the non-contact phase-locked and self-injection-locked vital sign sensor of claim 9, wherein the frequency divider, the phase detector and the charge pump are integrated into an integrated circuit, the integrated circuit is furnished with a plurality of leads to electrically couple the signal-processing device, and the signal-processing device controls the integrated circuit through a transmission interface.

* * * * *